(12) United States Patent
Eviston

(10) Patent No.: US 11,857,554 B2
(45) Date of Patent: Jan. 2, 2024

(54) DRUG DELIVERY DEVICE WITH PRE-ASSEMBLED CARTRIDGE

(71) Applicant: Intravital Pty Ltd., Randwick (AU)

(72) Inventor: Timothy J. Eviston, Randwick (AU)

(73) Assignee: INTRAVITAL PTY LTD., New South (GB)

( * ) Notice: Subject to any disclaimer, the term of this patent is extended or adjusted under 35 U.S.C. 154(b) by 233 days.

(21) Appl. No.: 15/577,999

(22) PCT Filed: Jun. 2, 2016

(86) PCT No.: PCT/AU2016/050444
§ 371 (c)(1),
(2) Date: Nov. 29, 2017

(87) PCT Pub. No.: WO2016/191819
PCT Pub. Date: Dec. 8, 2016

(65) Prior Publication Data
US 2018/0154080 A1    Jun. 7, 2018

(30) Foreign Application Priority Data

Jun. 2, 2015  (AU) ................................. 2015902089
Jul. 7, 2015  (AU) ................................. 2015902669
Aug. 3, 2015  (AU) ................................. 2015903087

(51) Int. Cl.
*A61M 5/178*     (2006.01)
*A61K 31/573*    (2006.01)
(Continued)

(52) U.S. Cl.
CPC .......... *A61K 31/573* (2013.01); *A61F 9/0008* (2013.01); *A61K 9/0024* (2013.01);
(Continued)

(58) Field of Classification Search
CPC ............ A61M 5/2422; A61M 5/31595; A61M 5/2466; A61M 5/2033; A61M 5/1452;
(Continued)

(56) References Cited

U.S. PATENT DOCUMENTS 2,221,739 A    11/1940  Reiter
2,669,230 A    2/1954   Smoot
(Continued)

FOREIGN PATENT DOCUMENTS

CN    101500630 A    8/2009
CN    102869399 A    1/2013
(Continued)

OTHER PUBLICATIONS

International Search Report dated Aug. 24, 2016 (4 pages) from PCT priority Application No. PCT/AU2016/050444.
(Continued)

*Primary Examiner* — Nathan R Price
*Assistant Examiner* — Tania Ismail
(74) *Attorney, Agent, or Firm* — Crowell & Moring LLP; John C. Freeman

(57) ABSTRACT

A delivery device for delivering a gel or liquid pharmaceutical to a treatment site, the delivery device including a body extending from a delivery tip, the body defining a cavity for retaining a pharmaceutical or a pre-assembled cartridge holding the pharmaceutical; and a driver for mechanically discharging the pharmaceutical from the cartridge to the delivery tip. The driver may be adapted to release a consistent flow of the pharmaceutical. In addition, the delivery device may be biased into a release configuration.

18 Claims, 13 Drawing Sheets

(51) Int. Cl.

| | |
|---|---|
| *A61M 5/48* | (2006.01) |
| *A61F 9/00* | (2006.01) |
| *A61K 9/00* | (2006.01) |
| *A61M 5/315* | (2006.01) |
| *A61M 5/142* | (2006.01) |
| *A61M 5/24* | (2006.01) |
| *A61K 47/36* | (2006.01) |
| *A61B 17/34* | (2006.01) |
| *A61M 5/31* | (2006.01) |
| *A61M 39/18* | (2006.01) |
| *A61M 5/00* | (2006.01) |
| *A61M 5/145* | (2006.01) |
| *A61M 5/20* | (2006.01) |
| *A61B 90/00* | (2016.01) |

(52) U.S. Cl.
CPC ......... *A61K 47/36* (2013.01); *A61M 5/14248* (2013.01); *A61M 5/24* (2013.01); *A61M 5/2422* (2013.01); *A61M 5/31565* (2013.01); *A61M 5/31595* (2013.01); *A61M 5/48* (2013.01); *A61B 17/3472* (2013.01); *A61B 2090/3933* (2016.02); *A61B 2090/3941* (2016.02); *A61B 2505/05* (2013.01); *A61M 5/145* (2013.01); *A61M 5/1452* (2013.01); *A61M 5/2033* (2013.01); *A61M 5/2466* (2013.01); *A61M 5/315* (2013.01); *A61M 5/3158* (2013.01); *A61M 5/31501* (2013.01); *A61M 5/31581* (2013.01); *A61M 39/18* (2013.01); *A61M 2005/005* (2013.01); *A61M 2005/2477* (2013.01); *A61M 2005/2481* (2013.01); *A61M 2005/3117* (2013.01); *A61M 2205/0266* (2013.01); *A61M 2205/13* (2013.01); *A61M 2205/586* (2013.01); *A61M 2205/8206* (2013.01)

(58) Field of Classification Search
CPC .............. A61M 5/145; A61M 5/31501; A61M 5/3158; A61M 5/31581; A61M 2005/2481; A61M 2005/2477
See application file for complete search history.

(56) References Cited

U.S. PATENT DOCUMENTS

| | | | |
|---|---|---|---|
| 3,496,937 | A | 2/1970 | Balson |
| 4,444,560 | A | 4/1984 | Jacklich |
| 4,641,766 | A * | 2/1987 | Vlasich .................. A61M 3/00 222/391 |
| 4,659,327 | A | 4/1987 | Bennett et al. |
| 8,574,199 | B2 | 11/2013 | von Bülow et al. |
| 9,061,104 | B2 | 6/2015 | Daniel |
| 9,623,188 | B2 | 4/2017 | Nielsen et al. |
| 2009/0254043 | A1 | 10/2009 | Van Bülow et al. |
| 2009/0264828 | A1 | 10/2009 | Dette |
| 2011/0166512 | A1 | 7/2011 | Both |
| 2012/0041379 | A1 | 2/2012 | Macarthur |
| 2012/0041384 | A1 | 2/2012 | Finke |
| 2013/0144218 | A1 | 6/2013 | Daniel |
| 2013/0211330 | A1 | 8/2013 | Pedersen |
| 2014/0194825 | A1 | 7/2014 | Nielsen et al. |
| 2014/0290792 | A1 | 10/2014 | Avery et al. |
| 2015/0080810 | A1 | 3/2015 | Hendersen et al. |
| 2015/0202366 | A1 | 7/2015 | Hendersen et al. |

FOREIGN PATENT DOCUMENTS

| | | | |
|---|---|---|---|
| CN | | 103153367 A | 6/2013 |
| CN | | 103702699 A | 4/2014 |
| CN | | 104379195 A | 2/2015 |
| CN | | 104582763 A | 4/2015 |
| WO | WO | 2008/003560 A1 | 1/2008 |
| WO | WO | 2011/112136 A1 | 9/2011 |
| WO | WO | 2012/020084 A2 | 2/2012 |
| WO | WO | 2013/004844 A1 | 1/2013 |
| WO | WO | 2013/160152 A1 | 10/2013 |
| WO | WO | 2014/005954 A1 | 1/2014 |

OTHER PUBLICATIONS

Written Opinion dated Aug. 24, 2016 (6 pages) from PCT priority Application No. PCT/AU2016/050444.
International Preliminary Report on Patentability dated Oct. 4, 2017 (18 pages) from PCT priority Application No. PCT/AU2016/050444.
Extended European Search Report (7 pages) dated Jan. 21, 2019 from corresponding EP Application No. 16802249.9.
Office Action dated Mar. 24, 2021 (6 pages, foreign text) from corresponding Chinese Patent Application No. 201680032292.4.

* cited by examiner

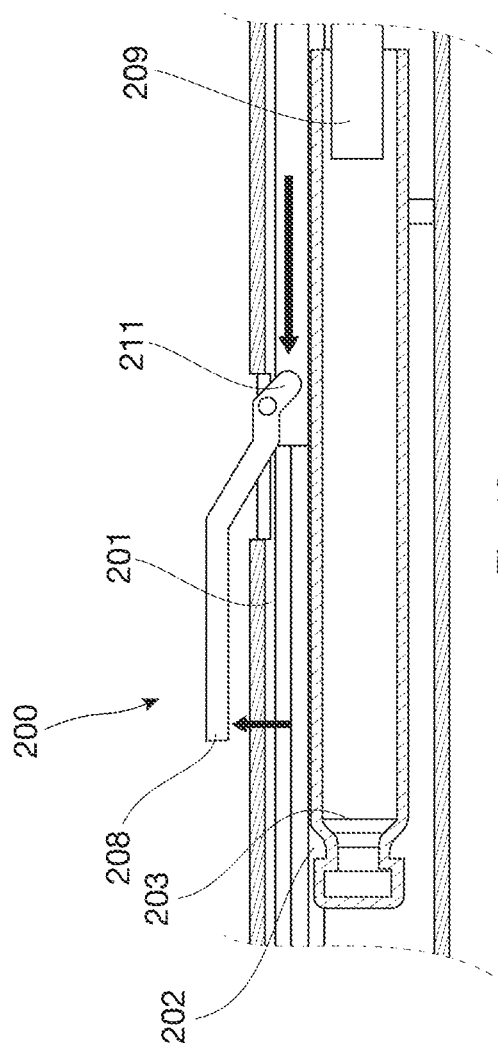
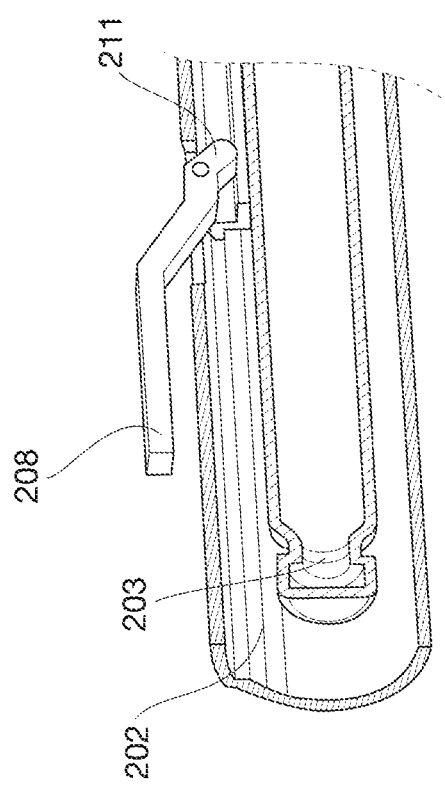

DRUG DELIVERY DEVICE WITH PRE-ASSEMBLED CARTRIDGE

This application claims priority to International Application No. PCT/AU2016/050444 filed Jun. 2, 2016;Australian Application No. 2015902089 filed Jun. 2, 2015;Australian Application No. 2015902669 filed Jul. 7, 2015; and Australian Application No. 2015903087 filed Aug. 3, 2015; the entire contents of each are incorporated herein by reference.

BACKGROUND

The present invention relates to a delivery device for delivering a therapeutic substance in a liquid or gel form.

SUMMARY

Disclosed in some forms is a delivery device for delivering a gel or liquid pharmaceutical to a treatment site, the delivery device comprising a body extending from a delivery tip, the body defining a cavity for retaining a the pharmaceutical or a pre-assembled cartridge holding the pharmaceutical; and a driver for mechanically discharging the pharmaceutical from the cartridge to the delivery tip. In some forms the driver is adapted to release a consistent flow of the pharmaceutical. In some forms the delivery device is biased into a release configuration.

Delivery of a therapeutic substance in a liquid or gel form is complicated by the need for sterile supply of therapeutic substances. It is therefore desirable to maintain the therapeutic substance in a sealed capsule for use, in a way that does not break the sterile supply.

Further, the viscosity of the liquid or gel means delivery can be inconsistent or difficult, particularly when manually controlled by the user. It is desirable to have continuous, predictable and controlled release of the liquid or gel with low levels of variation for different users. When a viscous substance is delivered, the initial inertia on the plunger can require significant force from a user or can mean that the initial dispensing is rushed or unpredictable.

The device provides for improved delivery of the therapeutic substance, improved consistency, greater ease for the doctor or other user. In some forms delivery of the drug beyond a selected site is minimised.

Further, surgical nerve injury peripheral to the surgery is a danger of surgery. Nerve dysfunction can result from trauma to the nerves despite the nerves appearing to be intact. This makes nerve dysfunction difficult to predict during surgery. Traumatic mechanisms such as stretch, thermal injury, electrical injury, compression and ischaemia can accumulate to cause activation of pathways of cellular degradation within a nerve's axon. This can cause nerve break down and loss of function.

BRIEF DESCRIPTION OF THE FIGURES

FIG. 13 shows a cutaway detail of the embodiment of FIG. 12;

FIG. 14 shows a perspective cutaway detail of the embodiment of FIG. 12.

DETAILED DESCRIPTION OF EMBODIMENTS OF THE DISCLOSURE

Figure 1:
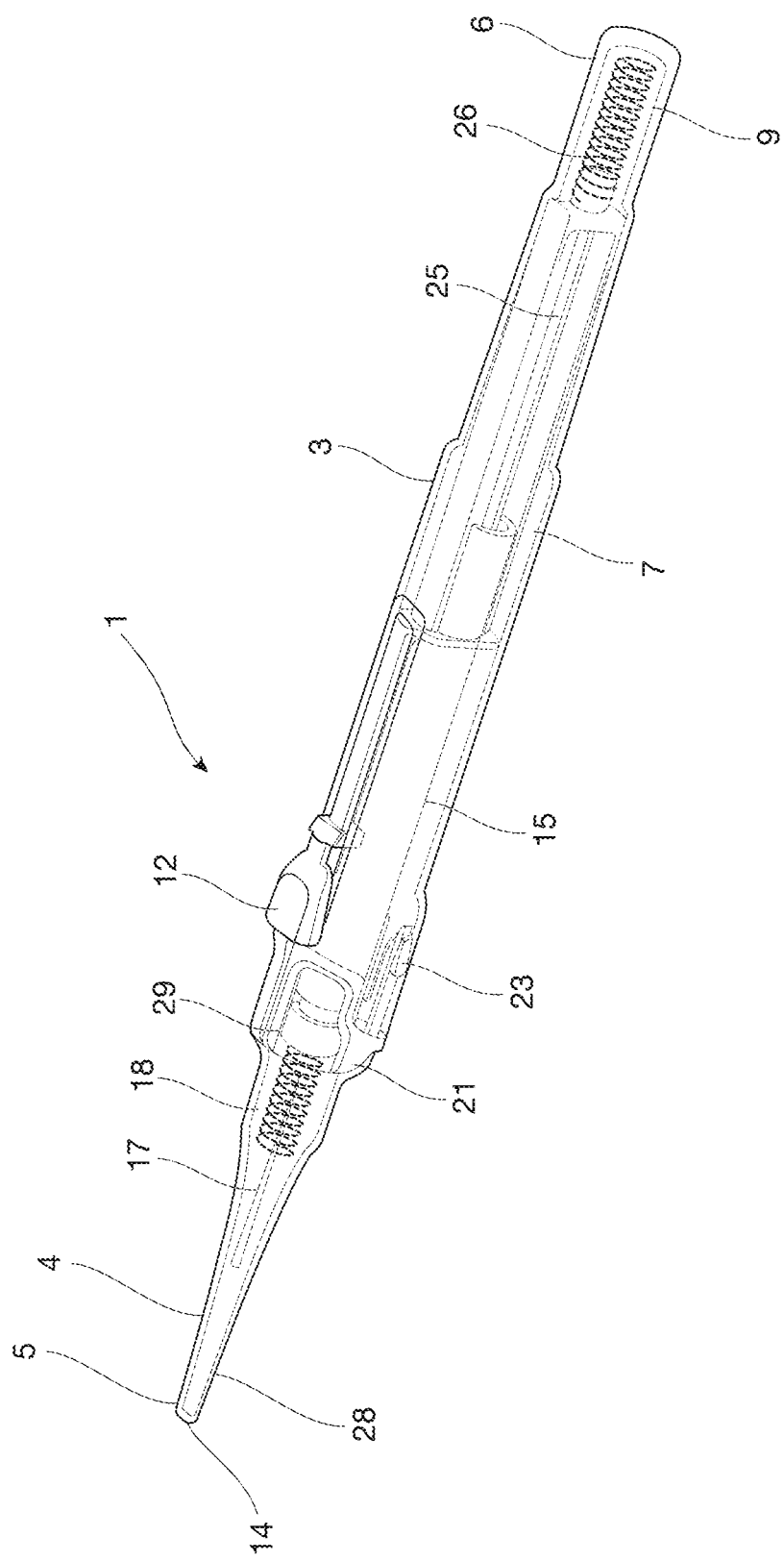
FIG. 1 shows a front top perspective view of one embodiment of the delivery device.

Disclosed in some forms is a delivery device for delivering a gel or liquid pharmaceutical to a treatment site, the delivery device comprising a body extending from a delivery tip, the body defining a cavity for retaining a pre-assembled cartridge holding the pharmaceutical; and a driver for mechanically discharging the pharmaceutical from the cartridge to the delivery tip.

In some forms the device further comprises a perforator for creating an opening in the cartridge to allow for discharge of the pharmaceutical from the cartridge to the delivery tip. In some forms the perforator is a manual perforator. In some forms the perforator acts by relative movement of the cartridge and the perforator. In some forms the perforator comprises a needle positioned proximal the delivery tip.

In some forms the cartridge and perforator are relatively moveable between a sealed configuration and an active configuration in which the cartridge is perforated.

In some forms movement of the cartridge and the perforator into the active configuration is activated by a manual activator.

In some forms the driver is adapted to release a consistent flow of the pharmaceutical. In some forms the driver has a ratchet action.

In some forms the device further includes an actuator for actuating the driver. In some forms actuation of the actuator releases causes the driver to drive motion of a displaceable plunger, the plunger being configured to move such that the pharmaceutical is discharged from the cartridge to the tip.

In some forms the driver is in the form of a pretensioned spring.

In some forms the device further includes a brake adapted to retain the plunger with respect to the cartridge.

In some forms the delivery tip comprises a replaceable portion to allow for variation of tip size and shape configurations.

In some forms the device is adapted for single use. In some forms the device is sized and configured for single hand use.

Further disclosed is a method of treatment during surgery comprising applying a gel or liquid pharmaceutical to a treatment site exposed during surgery using the delivery device described above.

In further aspects, disclosed is a device for applying a therapeutic substance to a nerve, the device comprising a reservoir adapted to contain the therapeutic substance, an outlet and a plunger, the plunger being biased to adopt a release motion in which the therapeutic substance is expelled from the reservoir through the outlet, the plunger being retained relative to the reservoir by a retainer.

In some forms the outlet comprises a tip, the tip being removable from the device to allow interchange with one or more alternative tips having different dimensions.

In some forms the rate of release of the therapeutic substance is controlled.

The device allows for supply of the therapeutic substance without interrupting sterile supply or perforating the cartridge until the time of use. It also allows for continuous predictable delivery which is not reliant upon manual actuation so has a decreased variability between users and greater consistency of application. In some forms the tip allows for a variety of tip designs for different uses.

The device and process may provide for improved levels of pain, improved recovery, improved muscle function, improved autonomy, or improved sensation. In some forms chronic pain or inflammation can be reduced or avoided.

In some forms the therapeutic substance comprises a formulation comprising a biodegradable carrier and a therapeutic ingredient.

In some forms the therapeutic ingredient comprises a local anaesthetic.

In some forms the therapeutic ingredient comprises an anti-inflammatory agent.

In some forms the therapeutic ingredient comprises an antibiotic.

In some forms the therapeutic substance is selected from substances that can intervene in the activation of pathways of cellular degradation within the nerve.

Positioning of a therapeutic substance during surgery allows for work around vital structures.

The device allows controlled, predictable and continuous application of a therapeutic substance in the form of a liquid or a gel directly to a location for treatment such as a nerve, a burn site, a surgical site or a cancer. The device can limit or prevent peripheral damage, trauma or injury occurring during treatment and peripheral delivery of the therapeutic substance beyond the intended site.

In some forms the therapeutic substance comprises a carrier, which is in some forms, adapted to slow release, to prolong the pharmacokinetics of the active pharmaceutical, and to reduce dissemination of the active pharmaceutical ingredient beyond the site at which its effect is intended. This provides greater concentration of the active pharmaceutical to the relevant cells and limits waste.

The device has been described for treatment of burns, cancer or surgery. However it will be clear that the device can be utilised beyond the described circumstances.

Referring now to the Figures, FIG. 1 shows a perspective view of one embodiment of a delivery device 1.

The delivery device 1 comprises a body 3 extending from a tip 4 at a leading end 5 to a trailing end 6. The body 3 is configured to define an interior retaining cavity 6 within the body, along with a spring cavity 9, also within the body.

The delivery device 1 further includes an actuator 12 located outwardly of the body 3.

The tip 4 is a delivery tip and includes an outlet 14 positioned at the leading end of the tip 4. The outlet 14 is adapted to allow discharge of a liquid or gel.

The retaining cavity 7 is configured to retain a cartridge 15 within the cavity. The cartridge contains a therapeutic substance (not illustrated) in the form of a liquid or gel.

The cartridge 15 comprises a prefilled cartridge composed, for example, of glass or plastic and sterilised for use.

Once the cartridge 15 is sterilised, it is critical to maintain sterility.

The tip includes a perforator 17 in the form of a perforating needle composed of stainless steel. The perforator 17 is maintained within a tip cavity 18 within the tip 4.

A tip spring 19 is also retained within the tip cavity 18. The tip spring 19 acts to separate the cartridge 15 from the perforator 17 to maintain the sterility of the cartridge until opening is required. In another form the cartridge may be separated from the perforating needle by a "crown" of polycarbonate fingers which can be overcome by the activation of the device.

The tip cavity 18 is in communication with the retaining cavity by means of a neck portion 21. The neck portion 21 is hollow and includes ribs such that in a disassembled state the cartridge can be correctly aligned with the needle.

In the illustrated form the tip 4 is removable from the body 3 and the device 1 includes a release clip 23 which allows removal of the tip 4 for reloading of cartridges.

A plunger 25 is located within the retaining cavity 7. The plunger 25, in use, acts upon the cartridge 15 to discharge the therapeutic substance from the cartridge into the outlet 14. The plunger, in the illustrated form, surrounds the cartridge 15 to hold it in place while the plunger 25 pushes the contents of the cartridge 15 out of the cartridge and through the outlet 14.

The plunger 25 is powered by a plunger spring 26 which is located in the plunger cavity 9 of the body 3. In the illustrated form, the plunger spring 26 is locked in place by, for example, a pin, until the device is armed for use.

The plunger 25 acts directly on the cartridge 15 to discharge the contents.

In use, an operator actuates the device 1 by depressing the actuator 12. The actuator 12 is a button connected to a gate or ratchet which allows the release of the pretensioned plunger spring 26.

In some forms that actuator is in the form of a brake and release can be controlled by releasing the actuator 12 again and allowing the brake actuator to act to restrain the discharge. In some forms the brake configuration is a twist grip or a ratchet controlled twisting grip, a tilting slit, a toothed ratchet or a lever and spring. The braking force may be increased by using a spring under the button actuator to actively engage the braking mechanism upon release of the button by the user.

The cartridge contacts the perforator 17 to perforate the cartridge, creating an opening for release of the therapeutic substance within the cartridge.

The tip 4 in some forms comprises an interchangeable end portion 28. This allows either changing of the tip dimensions and configuration to best suit the use. Further the tip 4 can include an attachment such as a luer lock to allow connection to standard needle, intravenous or canula configurations.

Figure 2:
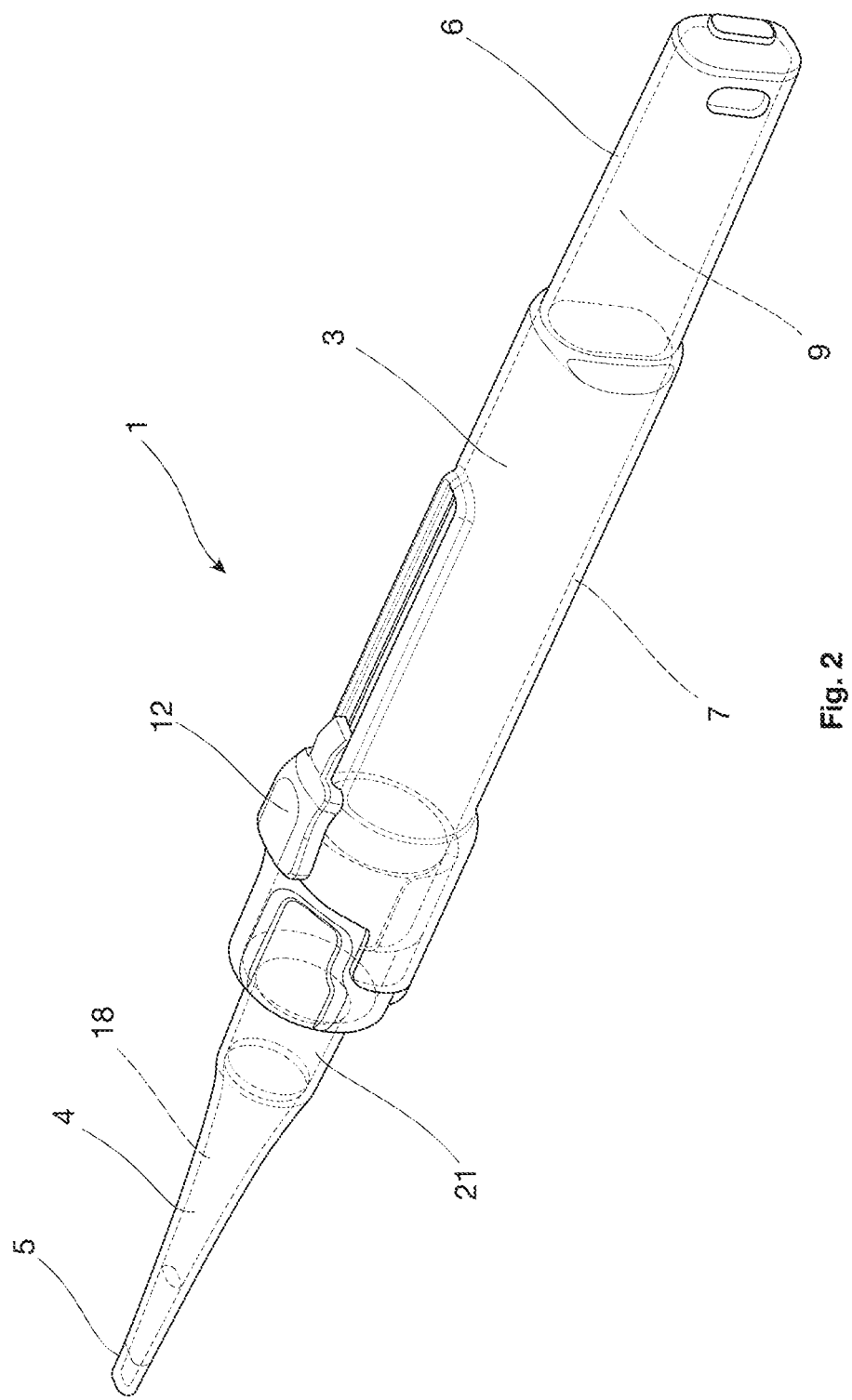
FIG. 2 shows a rear top perspective view of the body of the delivery device of FIG. 1.
Figure 3:
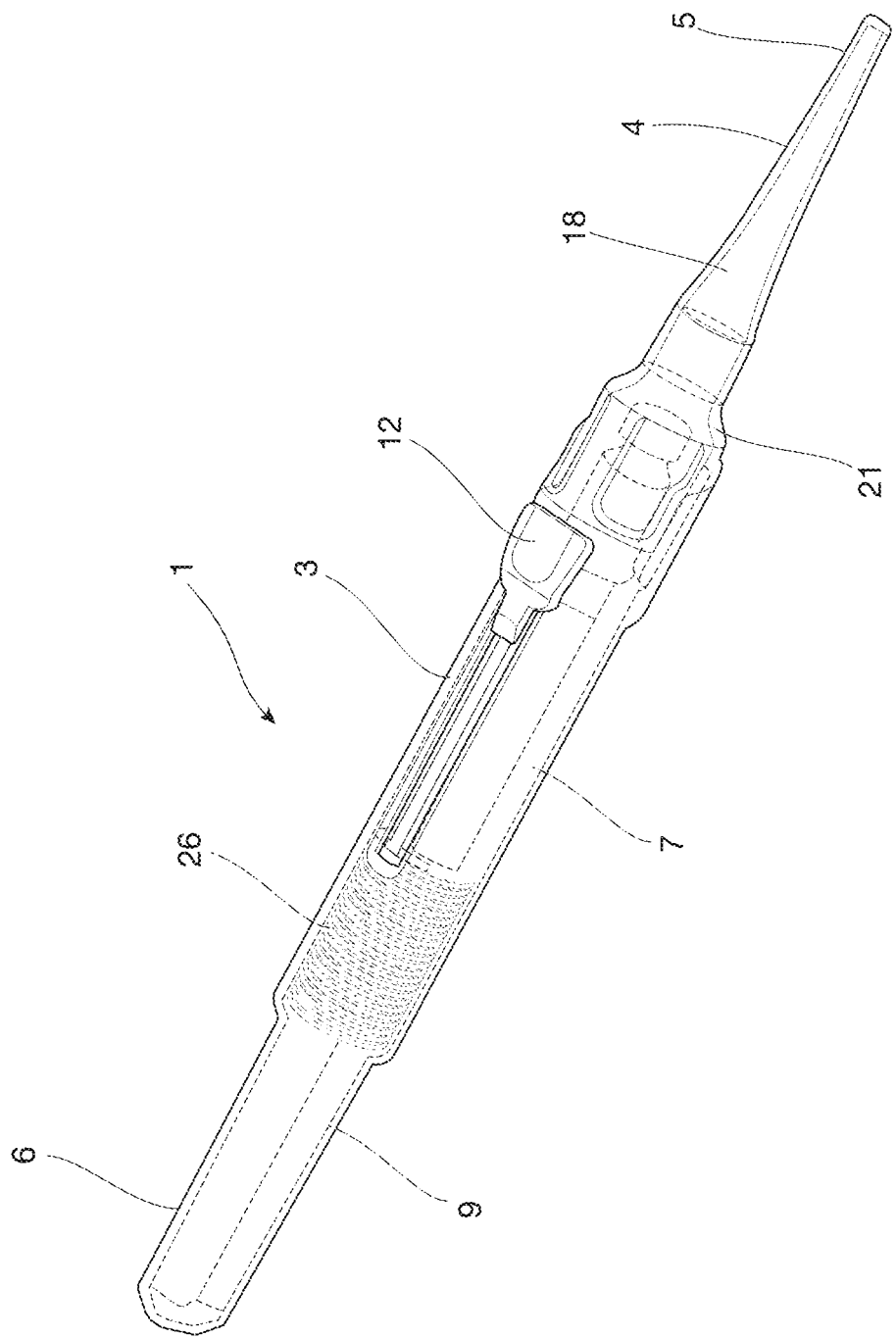
FIG. 3 shows a top view of the delivery device of FIG. 1.
Figure 4:
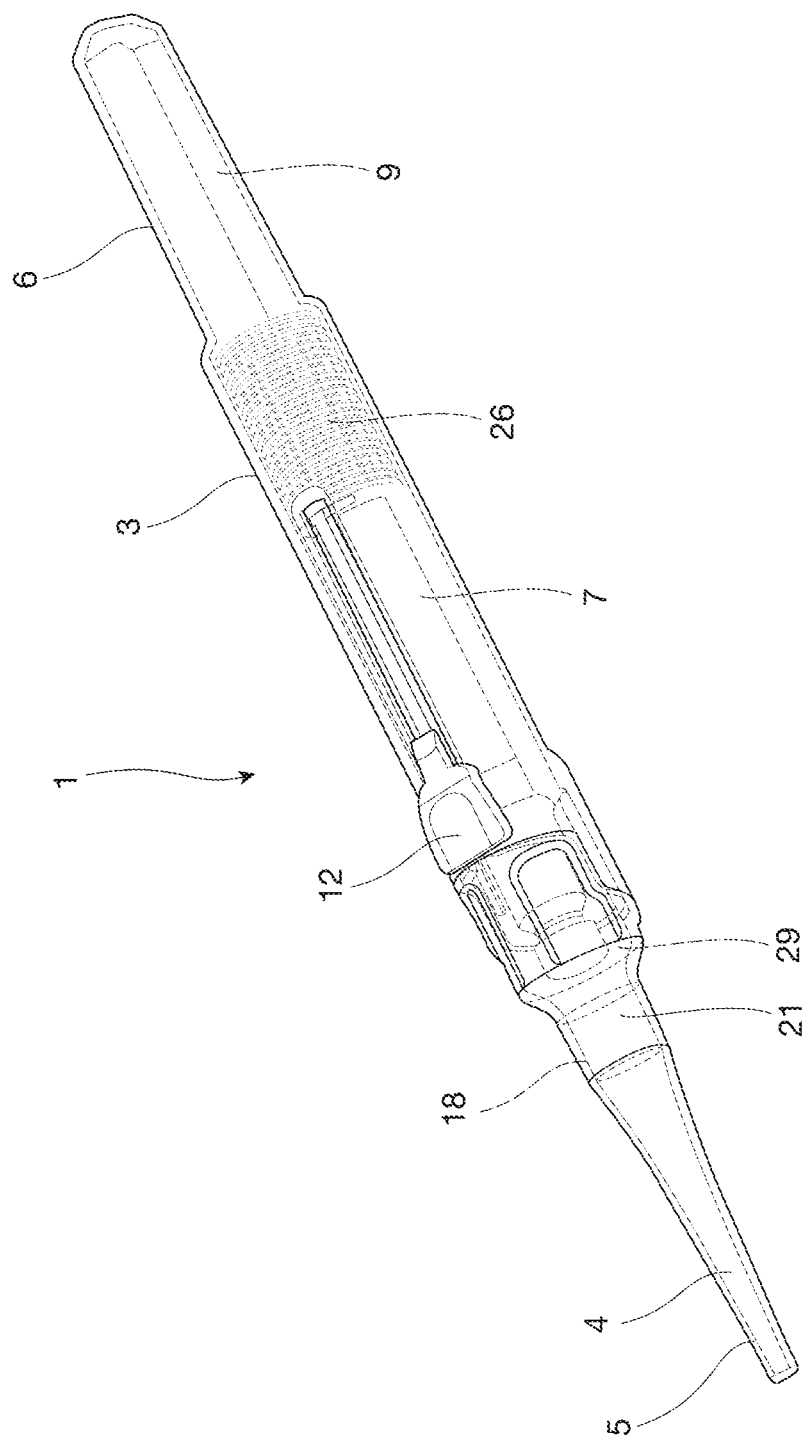
FIG. 4 shows a top partially translucent view of the delivery device of FIG. 1.
Figure 5:
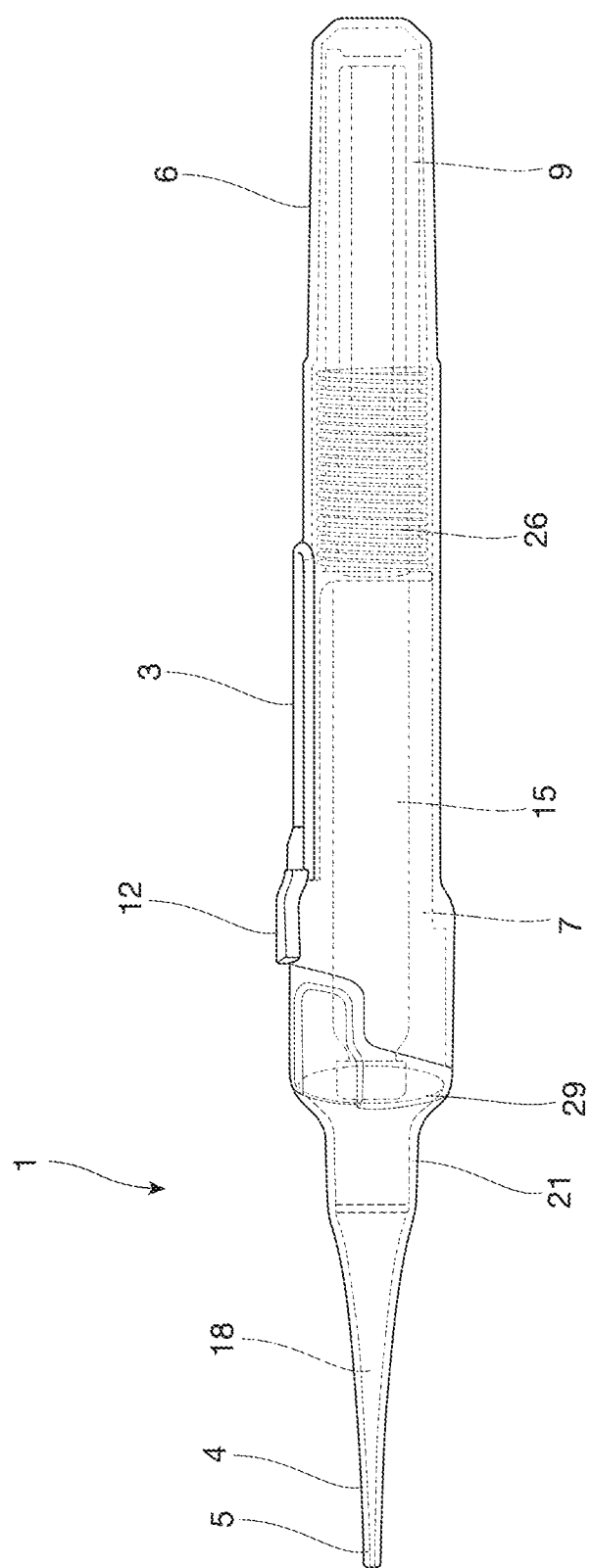
FIG. 5 shows a side partially translucent view of the delivery device of FIG. 1.
Figure 6:
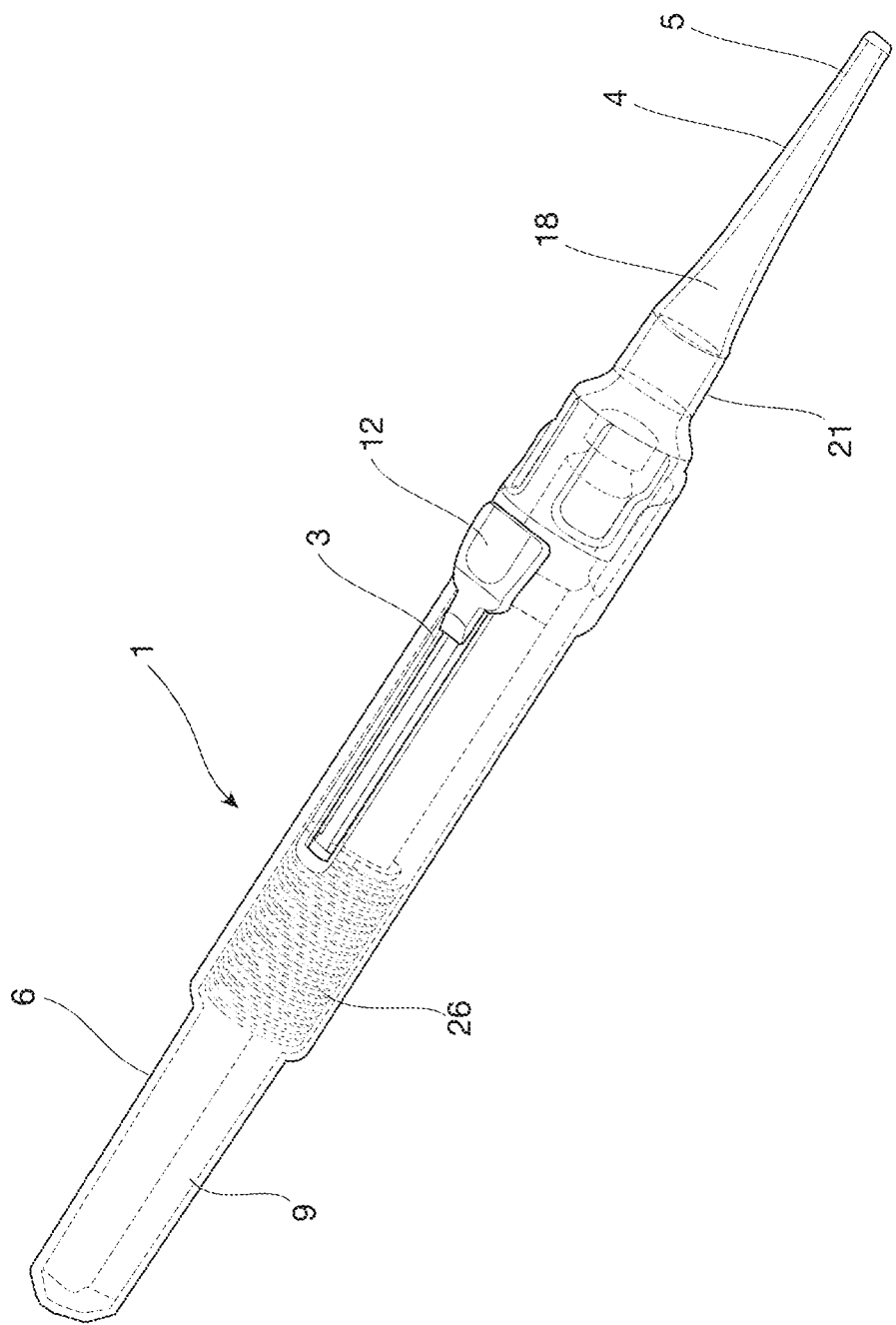
FIG. 6 shows a top perspective partially phantom view of the delivery device of FIG. 1.
Figure 7:
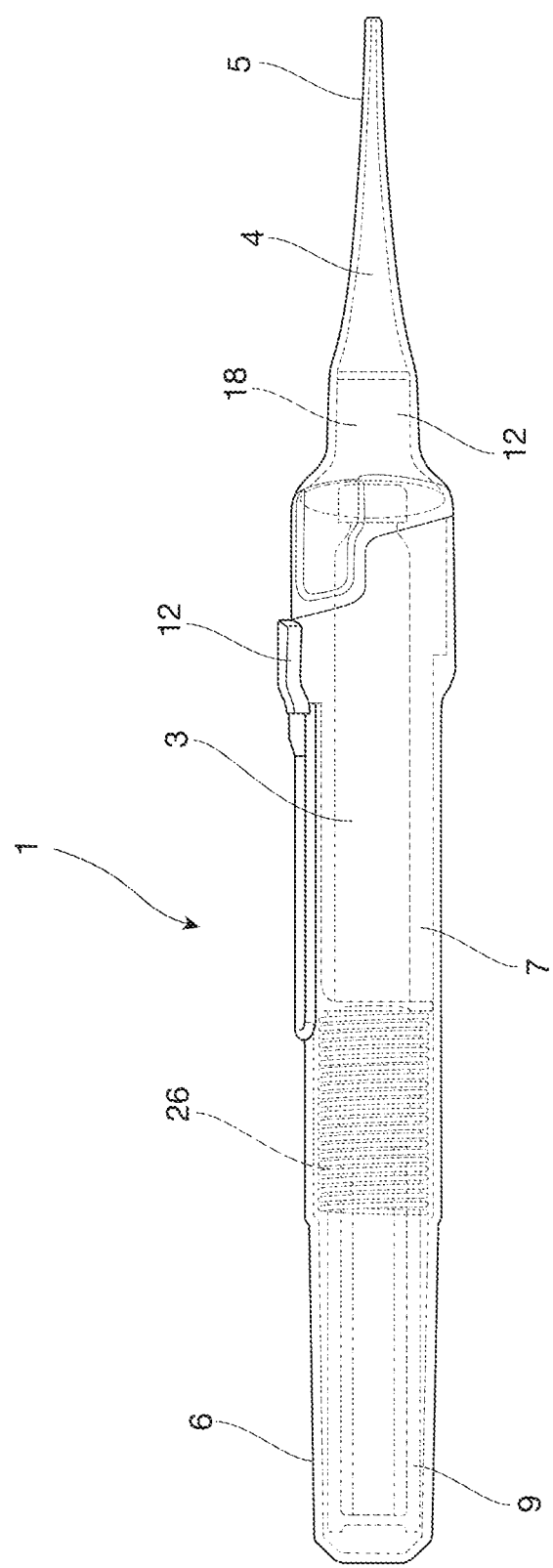
FIG. 7 shows a side perspective partially phantom view of the delivery device of FIG. 1.
Figure 8:
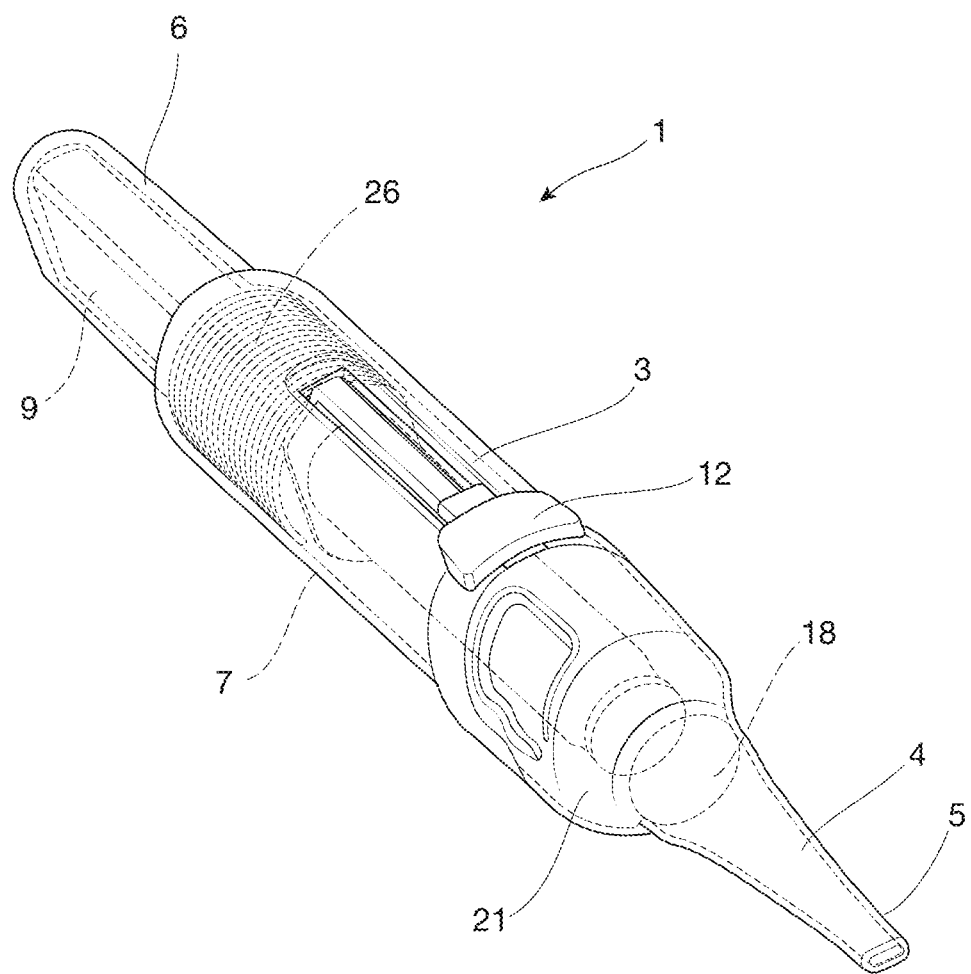
FIG. 8 shows a front perspective view of the delivery device of FIG. 1.

Turning now to FIG. 2, the device body 3 and tip 4 are composed of plastic and are configured such that the retaining cavity 7, the spring cavity 9, the tip cavity 18 and the neck portion 21 for a single joined cavity extending through the device 1. The cavity includes a plunger shoulder 29 positioned to limit the movement of the plunger toward the trailing end.

As shown in FIGS. 3 through 8, the delivery device body 3 extends from the tip 4 to the trailing end. In this form, the spring 26 is positioned at a wider portion of the body to allow a larger calibre spring in an embodiment of the design which has a shorter overall profile. In this configuration the spring aids in maintaining the plunger in position with regards to the contained cartridge.

The actuator is adapted to ratchet so that the spring 26 acts on the plunger 25 when the actuator button is actuated.

In the illustrated form the tip 4 is removable from the body 3 and the device 1 includes a release clip 23 which allows removal of the tip 4 for reloading of cartridges. Alternative tips may include integrated LEDs, a long, thin, curved nozzle for specific fine applications, a spray nozzle for wider surface area applications, a luer lock or similar tip for connection to a standard IV drip, cannula or needle, a pliable tip for endoscopy or laparoscopy.

A plunger 25 is located within the retaining cavity 7. The plunger 25, in use, acts upon the cartridge 15 to discharge the therapeutic substance from the cartridge into the outlet 14. The plunger, in the illustrated form, surrounds the cartridge 15 to hold it in place while the plunger 25 pushes the contents of the cartridge 15 out of the cartridge and through the outlet 14.

The plunger 25 is powered by a plunger spring 26 which is located in the plunger cavity 9 of the body 3. In the illustrated form, the plunger spring 26 is locked in place by, for example, a pin, until the device is armed for use.

The plunger 25 acts directly on the cartridge 15 to discharge the contents.

In use, an operator actuates the device 1 by depressing the actuator 12. The actuator 12 is a button connected to a gate or ratchet or similar braking mechanism which allows the release of the pretensioned spring. In some forms that actuator is in the form of a brake and release can be controlled by releasing the actuator 12 again and allowing the brake actuator to act to restrain the discharge. In some forms the rate of release can be adjusted by a user by utilising the brake.

The cartridge contacts the perforator 17 to perforate the cartridge, creating an opening for release of the therapeutic substance within the cartridge.

The device is configured for use with a single hand. This comprises having a slender device with a fine motor or a pen grip. The actuator or braking mechanism allows a user to control the discharge without requiring the user to apply significant pressure to effect manual discharge. The user can therefore control a continuous or consistent rate of delivery using this grip without significant strain. The device also allows the continuous and consistent release of therapeutic without the user applying pressure or force beyond the activation of the actuator.

In some not illustrated forms, the device is activated for use by a twisting mechanism which moves the cartridge forward onto the perforating cannula. Alternatively the device is activated by removal of a restraining clip which allows the force of a spring to move the cartridge forward onto the cannula or by cocking forward of an external lever which moves the cartridge onto the cannula.

The accuracy of volume dispensing may be increased by using an adjustable actuator or electromechanical actuator (e.g. piezo-electric actuator), manually setting the limit of plunger movement inside or outside the device. optimising the plunger spring force and length or decreasing the caliber of the tip or canula or using a reservoir in series with the canula to limit flow rate for consistent or small volume dispensing, among other means.

The controlled rate of delivery may be may be further optimized by limiting the caliber of the internal canula/tip to restrict maximum flow, using opposed springs to even the force/time and force/distance characteristics of the spring, using a "constant force" spring, using an extension spring, a shape memory alloy, or using an electro-mechanical actuator eg. a piezoelectric actuator.

Further disclosed is a device for applying a therapeutic substance to a nerve, the device comprising a reservoir adapted to contain the therapeutic substance, an outlet and a plunger. In some forms the plunger is biased to adopt a release motion in which the therapeutic substance is expelled from the reservoir through the outlet, the plunger being retained relative to the reservoir by a retainer. In some forms the device further comprises an actuator, actuation of the actuator releasing the plunger to adopt a release motion and expel the therapeutic substance.

In some forms the outlet comprises a tip, the tip being removable from the device to allow interchange with one or more alternative tips having different dimensions.

In some forms the rate of release of the therapeutic substance is controlled.

Figure 9:
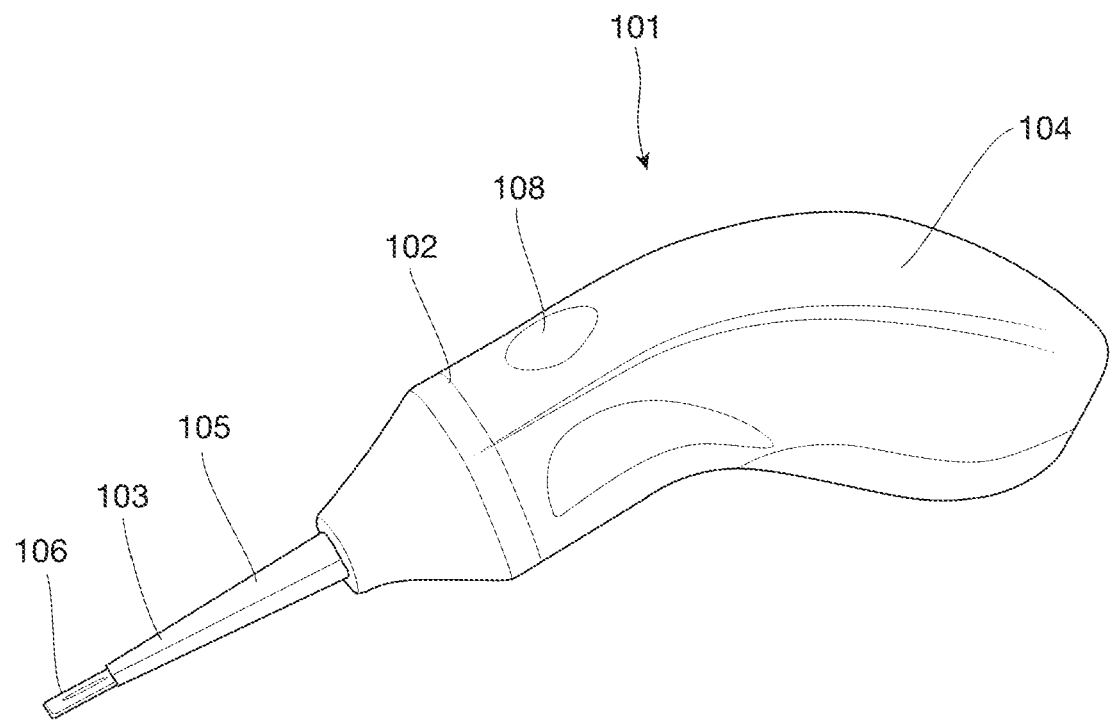
FIG. 9 shows a perspective view of a device of a second embodiment of the disclosure.
Figure 10:
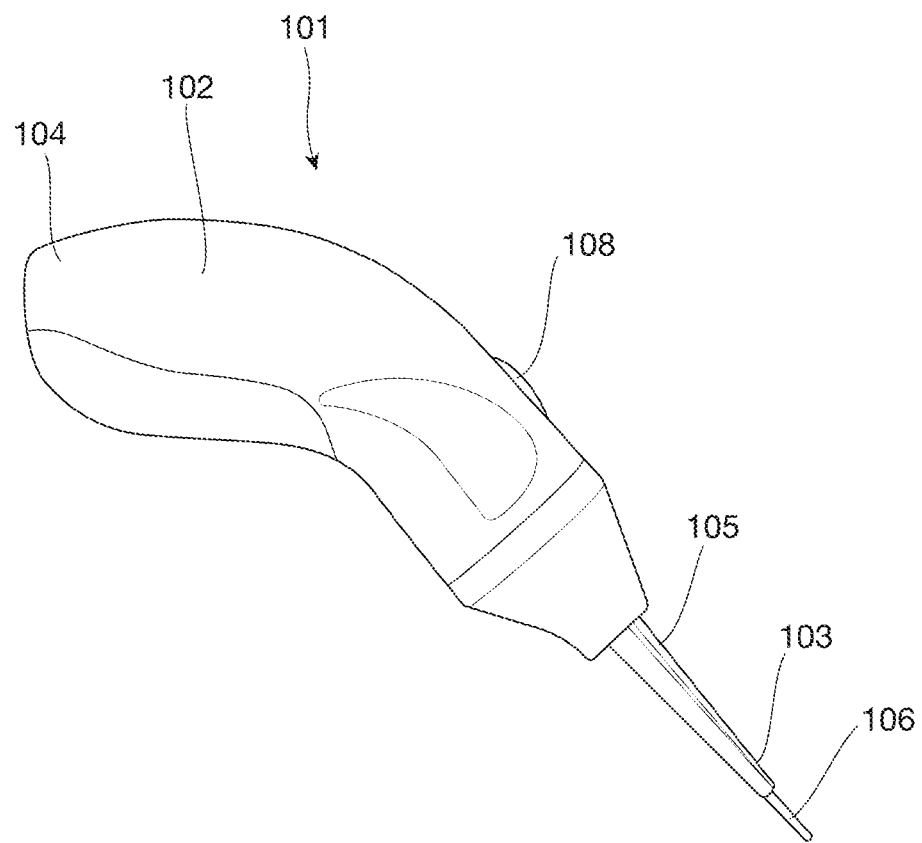
FIG. 10 shows a side view of the device of FIG. 9.
Figure 11:
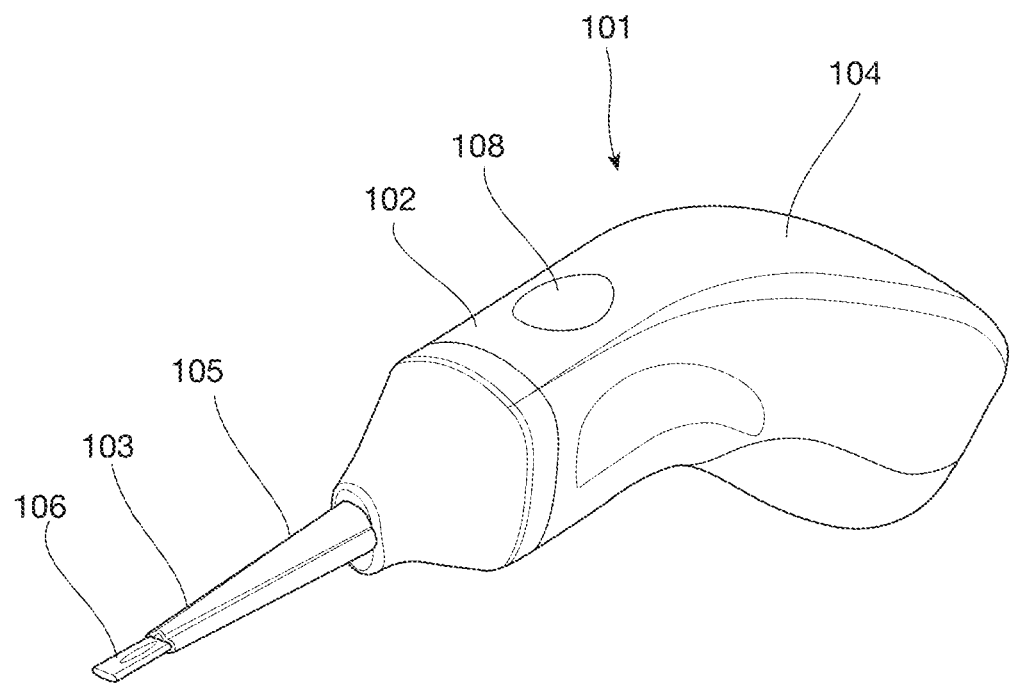
FIG. 11 shows a front perspective view of the device of FIG. 9.

Referring to FIGS. 9-11, disclosed is a delivery device for delivering a formulation.

The device is specifically described in relation to delivery of a formulation that can intervene in pathways of cellular degradation of a nerve. The device is specifically described for applying the formulation to a nerve directly. This limits trauma to the nerve or reduces the effects of that trauma on the nerve, thus providing for a lower likelihood of nerve dysfunction.

However it will be clear that the driver of the device can be utilised in alternative delivery devices.

The illustrated device 101 comprises a body 102 which is shaped to be held in an ergonomic manner in one hand. The body 102 contains a reservoir (not illustrated) in which a formulation is stored for use.

In some forms the formulation is held in a capsule in order to effect sterile delivery. The capsule is positioned within the body 102 for use.

The device 101 extends between a delivery end 103 and a rear end 104. The delivery end comprises a delivery conduit 105 extending from the body 102. The shape of the delivery end 103 and conduit 105 are elongate to allow for delivery of the formulation to a nerve during surgery when spaces can be compact and restrictive to movement.

The delivery end 103 further comprises a tip 106 which is shaped to allow accurate and precise delivery of the formulation to cells. The tip 106 is removable from the delivery end 103 to allow the tip 106 to be interchanged for a tip having a different dimension. This allows a surgeon to control the shape of the delivery, through changing aperture size and shape. The tip 106 is blunt to limit damage to the tissue and nerve.

In some forms, the tip dimensions are suited to different fields. For example, endoscopic surgery could utilise a long tip, microsurgery a fine tip and a curved tip could be utilised in applications that require the tip in a confined space. The tips 106 are selectable or interchangeable such that a single body can be provided with multiple tips for use.

In some forms the delivery end 103 and conduit 105 can also be shaped specifically for various surgical uses.

The device further includes an actuator 108 in the form of a button. Actuation of the actuator 108 by pressing the button causes the formulation to be released through the tip 106.

The reservoir of the interior of the body 102, includes a plunger (not illustrated) which is adapted to expel the formulation from the reservoir through the tip 106. The plunger is moveable with respect to the reservoir to perform this expulsion.

In one form, the plunger is biased toward the tip, that is, biased into a release motion that releases the formulation.

The plunger is biased by means of a pretensioned spring, pushing the plunger with respect to the reservoir.

In this form the plunger is held in position by a ratchet. Actuation of the actuator 108 causes the ratchet to release, allowing the plunger to move with respect to the reservoir, expelling formulation. The thickness of the formulation and the size of the tip and aperture maintain a consistent flow until the actuator is released at which stage the ratchet retains the plunger with respect to the reservoir again.

In some forms, the device is adapted for a single use application.

While the device has been described with a particular driver, it will be clear to a user that alternative drivers are available.

Figure 12:
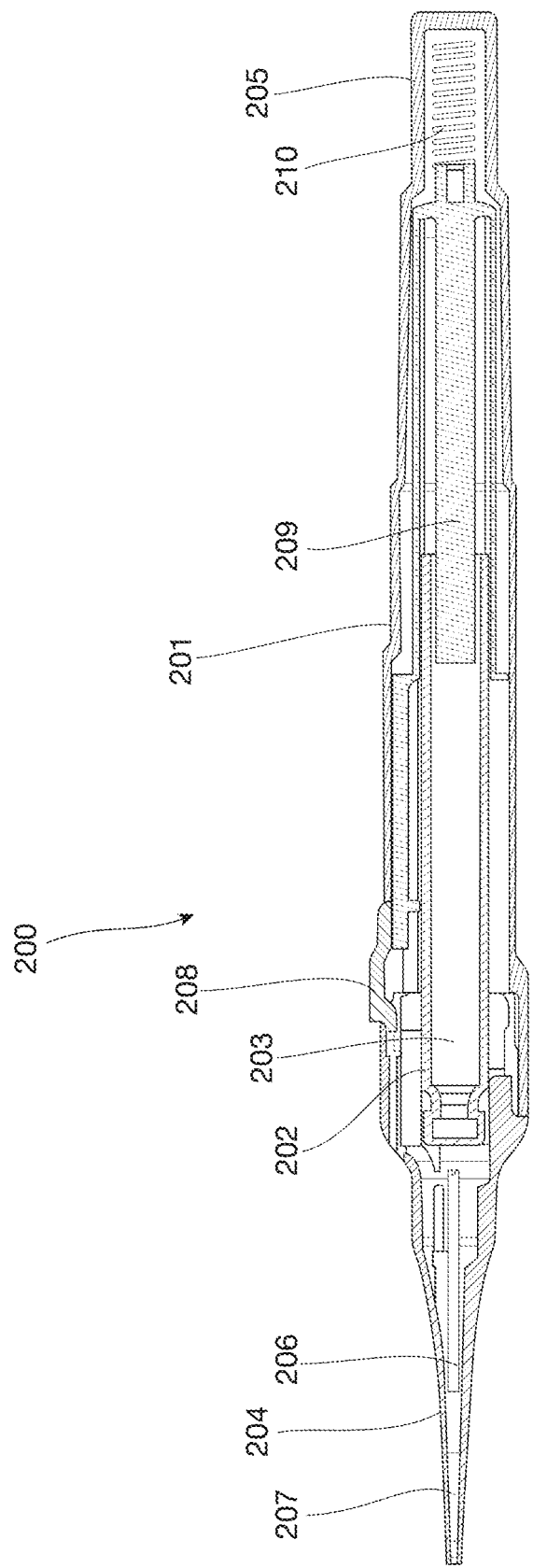
FIG. 12 shows a side cutaway view of a third embodiment of a delivery device of the disclosure.

Referring to FIGS. 12-14, the illustrated device 200 comprises a body 201 which is shaped to be held in an ergonomic manner in one hand. The body 201 contains a reservoir 202 in which a formulation is stored for use.

In the illustrated form the formulation is held in a capsule 203 in order to effect sterile delivery. The capsule is positioned within the body 201 for use.

The device 200 extends between a delivery end 204 and a rear end 205. The delivery end comprises a delivery conduit 206 extending from the body 201. The shape of the delivery end 204 and conduit 206 are elongate to allow for delivery of the formulation to a nerve during surgery when spaces can be compact and restrictive to movement.

The delivery end 204 further comprises a tip 207 which is shaped to allow accurate and precise delivery of the formulation to cells. In some forms the tip is removable from the delivery end to allow the tip to be interchanged for a tip having a different dimension. This allows a surgeon to control the shape of the delivery, through changing aperture size and shape. The tip 207 is blunt to limit damage to the tissue and nerve.

In some forms, the tip dimensions are suited to different fields. For example, endoscopic surgery could utilise a long tip, microsurgery a fine tip and a curved tip could be utilised in applications that require the tip in a confined space. The tips 207 are selectable or interchangeable such that a single body can be provided with multiple tips for use.

In some forms the delivery end 204 and conduit 206 can also be shaped specifically for various surgical uses.

The device further includes an actuator 208 in the form of a button. Actuation of the actuator 208 by pressing the button causes the formulation to be released through the tip 207.

The reservoir of the interior of the body 201, includes a plunger 209 which is adapted to expel the formulation from the reservoir through the tip 207. The plunger is moveable with respect to the reservoir to perform this expulsion.

In one form, the plunger is biased toward the tip, that is, biased into a release motion that releases the formulation. The plunger is biased by means of a pretensioned spring 210, pushing the plunger with respect to the reservoir.

In this form the plunger is held in position by a retaining member 211. Actuation of the actuator 208 causes the retaining member 211 to release, allowing the plunger 209 to move with respect to the reservoir 202, expelling formulation. The force of the spring, the thickness of the formulation and the size of the tip and aperture maintain a consistent flow until the actuator is released at which stage the retaining member 211 retains the plunger 209 with respect to the reservoir again. Accordingly, the distance traveled by the plunger 209, also known as the magnitude of release motion, is variable depending on the amount of time the retaining member 211 is in the release position, wherein the retaining member 211 is released from contact with the plunger 209.

In some forms the retaining member and actuator are integral to one another. In some forms the retaining member interacts frictionally with the plunger or a plunger extension to resist the forward movement of the plunger acted on by the spring. For example, as shown in FIG. 13, the retaining member 211 acts frictionally by solely engaging a smooth surface of the plunger 209.

In some forms, the device is adapted for a single use application.

The device is useable for a variety of purposes not limited to the delivery of a topical gel to an exposed structure such as a nerve, wound, muscle, bone, tumour or tumour bed, organ surface breach (eg. bowel anastomosis, dural tear, lung tear, lymph leak, vascular anastomosis), damaged surface or skin, the injection of a viscous or liquid substance subdermally, subcutaneously, intravenously etc, the controlled intraocular injection of a substance (into the eye), the controlled injection of a substance under radiological/imaging guidance such as facet joint, perineural or intra-articular injection or large surface topical application though using a spray tip.

It is to be understood that, if any prior art publication is referred to herein, such reference does not constitute an admission that the publication forms a part of the common general knowledge in the art, in Australia or any other country.

In the claims which follow and in the preceding description of the disclosure, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A delivery device for delivering a substance to a treatment site exposed during surgery, the delivery device comprising:

a body comprising an elongate delivery tip, wherein the body extends from a trailing end to a leading end, the leading end being blunt and comprising a structure to precisely deliver a substance topically to an exposed surface, the body defining a cavity for retaining a pre-assembled cartridge holding a substance;

a driver for mechanically discharging the substance from the cartridge to the delivery tip, a displaceable plunger biased toward the delivery tip by the driver to act upon the cartridge and adopt a release motion toward the delivery tip such that the displaceable plunger pushes the substance out of the cartridge, the driver acting upon the cartridge such that a portion of the displaceable plunger holds the cartridge in place by surrounding the cartridge on more than one side while the displaceable plunger pushes the substance of the cartridge out of the cartridge;

a brake mechanism integral to an actuator, which actuates movement of the driver to discharge the substance, the brake mechanism having a braking position in which a retaining member of the brake mechanism acts to restrain the release motion of the driver and a release position in which the brake mechanism does not act to restrain the release motion of the driver, the brake mechanism being movable from the braking position to adopt the release position and from the release position to adopt the braking position, wherein the retaining member acts frictionally on the driver to restrain the release motion of the driver as the driver moves.

2. The delivery device as defined in claim 1, further comprising a perforator for creating an opening in the cartridge to allow for discharge of the substance from the cartridge to the delivery tip.

3. The delivery device as defined in claim 2, wherein the perforator acts by relative movement of the cartridge and the perforator.

4. The delivery device as defined in claim 2, wherein the perforator comprises a needle positioned proximal the delivery tip.

5. The delivery device as defined in claim 2, wherein the cartridge and perforator are relatively movable between a sealed configuration and an active configuration in which the cartridge is perforated.

6. The delivery device as defined in claim 5, wherein movement of the cartridge and the perforator into the active configuration is activated by a manual activator.

7. The delivery device as defined in claim 1, wherein the driver is adapted to release a consistent flow of the substance.

8. The delivery device as defined in claim 1, wherein actuation of the actuator releases the brake mechanism.

9. The delivery device as defined in claim 8, wherein release of the brake mechanism allows the driver to drive motion of a displaceable plunger, the displaceable plunger being configured to move such that the substance is discharged from the cartridge to the delivery tip.

10. The delivery device as defined in claim 9, wherein the brake mechanism acts on the driver.

11. The delivery device as defined in claim 9, wherein the brake mechanism acts on the displaceable plunger.

12. The delivery device as defined in claim 1, wherein the retaining member acts frictionally by solely engaging a smooth surface of a displaceable plunger that is driven in motion by the driver.

13. The delivery device as defined in claim 1, wherein a magnitude of release motion is variable depending on the amount of time the braking mechanism is in the release position.

14. The delivery device as defined in claim 9, wherein the brake mechanism acts on the cartridge.

15. The delivery device as defined in claim 1, wherein at least a portion of the delivery tip is removable to allow for variation of size and shape configuration of the delivery tip.

16. The delivery device as defined in claim 1, wherein action of the driver moves the driver into the pre-assembled cartridge.

17. The delivery device as defined in claim 1, wherein the driver acts upon the cartridge such that during pushing of the substance by the driver results in a controlled delivery of the substance.

18. The delivery device as defined in claim 2, wherein the delivery device further comprises a tip spring, wherein the tip spring is retained within the cavity and acts to separate the cartridge from the perforator to maintain sterility of the cartridge.

* * * * *